(12) United States Patent
Wendler (10) Patent No.: US 9,345,441 B2
(45) Date of Patent: May 24, 2016

(54) APPARATUS AND METHOD FOR NUCLEAR IMAGING

(71) Applicant: SURGICEYE GMBH, Munich (DE)

(72) Inventor: Thomas Wendler, Munich (DE)

(73) Assignee: SURGICEYE GMBH, Munich (DE)

( * ) Notice: Subject to any disclaimer, the term of this patent is extended or adjusted under 35 U.S.C. 154(b) by 4 days.

(21) Appl. No.: 13/722,294

(22) Filed: Dec. 20, 2012

(65) Prior Publication Data

US 2013/0338490 A1 Dec. 19, 2013

(30) Foreign Application Priority Data

Dec. 20, 2011 (DE) .......................... 10 2011 121 708

(51) Int. Cl.
*A61B 6/00* (2006.01)
*A61B 1/317* (2006.01)
(Continued)

(52) U.S. Cl.
CPC .............. *A61B 6/466* (2013.01); *A61B 1/00045* (2013.01); *A61B 1/043* (2013.01);
(Continued)

(58) Field of Classification Search
CPC ........ A61B 5/415; A61B 5/417; A61B 5/418;
A61B 6/507; A61B 6/466; A61B 8/4245;
A61B 6/425; A61B 8/0841; A61B 6/4417;
A61B 1/307; A61B 1/233; A61B 6/56;
A61B 5/067; A61B 1/31; A61B 6/464;
A61B 6/483; A61B 1/2733; A61B 5/061;
A61B 1/043; A61B 1/3135; A61B 1/2736;
A61B 6/4258; A61B 1/227; A61B 1/2676;
A61B 6/5258; A61B 1/303; A61B 6/037;
A61B 1/063; A61B 6/481; A61B 1/0045;
A61B 1/317; A61B 8/4263; A61B 6/583;
A61B 8/5261; A61B 19/2203; A61B 2019/5291; A61B 19/5244; A61B 6/12;
A61B 8/12; G01T 1/161
USPC .................................... 600/407–436; 606/130
See application file for complete search history.

(56) References Cited

U.S. PATENT DOCUMENTS 6,212,423 B1 * 4/2001 Krakovitz ..................... 600/473
7,176,466 B2 * 2/2007 Rousso et al. ........... 250/370.08
(Continued)

FOREIGN PATENT DOCUMENTS

WO 2011038444 A1 4/2011

OTHER PUBLICATIONS

German Office Action, Patent Application: 102011121708.1, dated Nov. 16, 2012.
(Continued)

*Primary Examiner* — Sanjay Cattungal
(74) *Attorney, Agent, or Firm* — Patterson & Sheridan, LLP (57) ABSTRACT

A system for endoscopic nuclear imaging, a nuclear probe and related methods are provided. In one embodiment, a system includes a movable endoscopic nuclear probe which comprises a collimator and a detector, the endoscopic nuclear probe having an elongated body with a longitudinal axis (X), wherein the detector and the collimator are arranged on the elongated body, and the collimator having a field of view with an axis (Y) and the axis (Y) is angled with respect to the axis (X) of the elongated body of the endoscopic nuclear probe; means for determining the position and orientation of the elongated body of the endoscopic nuclear probe; an evaluation unit including means for computationally determining an actual position and actual orientation of the elongated body of the endoscopic nuclear probe; and a program storage section and means for computing at least one quality parameter of the image.

25 Claims, 7 Drawing Sheets

(51) Int. Cl.
| | |
|---|---|
| A61B 1/267 | (2006.01) |
| A61B 1/233 | (2006.01) |
| A61B 1/313 | (2006.01) |
| A61B 1/273 | (2006.01) |
| A61B 1/31 | (2006.01) |
| A61B 1/307 | (2006.01) |
| A61B 1/303 | (2006.01) |
| A61B 1/227 | (2006.01) |
| A61B 1/06 | (2006.01) |
| A61B 1/04 | (2006.01) |
| A61B 1/00 | (2006.01) |
| A61B 6/03 | (2006.01) |
| A61B 5/06 | (2006.01) |
| A61B 8/08 | (2006.01) |
| G01T 1/161 | (2006.01) |
| A61B 8/00 | (2006.01) |
| A61B 8/12 | (2006.01) |
| A61B 6/12 | (2006.01) |
| A61B 19/00 | (2006.01) |

(52) U.S. Cl.
CPC ............ *A61B 1/063* (2013.01); *A61B 1/227* (2013.01); *A61B 1/233* (2013.01); *A61B 1/2676* (2013.01); *A61B 1/2733* (2013.01); *A61B 1/2736* (2013.01); *A61B 1/303* (2013.01); *A61B 1/307* (2013.01); *A61B 1/31* (2013.01); *A61B 1/317* (2013.01); *A61B 1/3135* (2013.01); *A61B 5/061* (2013.01); *A61B 5/067* (2013.01); *A61B 6/037* (2013.01); *A61B 6/425* (2013.01); *A61B 6/4258* (2013.01); *A61B 6/4417* (2013.01); *A61B 6/464* (2013.01); *A61B 6/481* (2013.01); *A61B 6/483* (2013.01); *A61B 6/5258* (2013.01); *A61B 6/56* (2013.01); *A61B 8/0841* (2013.01); *A61B 8/4245* (2013.01); *G01T 1/161* (2013.01); *A61B 6/12* (2013.01); *A61B 6/583* (2013.01); *A61B 8/12* (2013.01); *A61B 8/4263* (2013.01); *A61B 8/5261* (2013.01); *A61B 19/2203* (2013.01); *A61B 19/5244* (2013.01); *A61B 2019/5291* (2013.01)

(56) References Cited

U.S. PATENT DOCUMENTS

| | | | | |
|---|---|---|---|---|
| 7,826,889 | B2 * | 11/2010 | David et al. | 600/436 |
| 8,000,773 | B2 * | 8/2011 | Rousso et al. | 600/436 |
| 8,606,349 | B2 * | 12/2013 | Rousso et al. | 600/436 |
| 8,909,325 | B2 * | 12/2014 | Kimchy et al. | 600/436 |
| 2003/0187349 | A1 | 10/2003 | Kaneko et al. | |
| 2004/0015075 | A1 * | 1/2004 | Kimchy et al. | 600/424 |
| 2004/0054248 | A1 * | 3/2004 | Kimchy et al. | 600/3 |
| 2004/0204646 | A1 | 10/2004 | Nagler et al. | |
| 2005/0205792 | A1 * | 9/2005 | Rousso et al. | 250/363.04 |
| 2006/0237652 | A1 * | 10/2006 | Kimchy et al. | 250/363.02 |
| 2007/0194241 | A1 * | 8/2007 | Rousso et al. | 250/369 |
| 2008/0042067 | A1 * | 2/2008 | Rousso et al. | 250/363.04 |
| 2008/0128626 | A1 * | 6/2008 | Rousso et al. | 250/362 |
| 2008/0230702 | A1 * | 9/2008 | Rousso et al. | 250/363.02 |
| 2008/0230705 | A1 * | 9/2008 | Rousso et al. | 250/363.04 |
| 2009/0259123 | A1 * | 10/2009 | Navab et al. | 600/424 |
| 2010/0266171 | A1 * | 10/2010 | Wendler et al. | 382/128 |
| 2014/0151563 | A1 * | 6/2014 | Rousso et al. | 250/362 |
| 2014/0163368 | A1 * | 6/2014 | Rousso et al. | 600/436 |

OTHER PUBLICATIONS

Extended European Search Report (EESR) on European Patent Application No. 12198715.0 mailed on Apr. 17, 2013.

* cited by examiner

APPARATUS AND METHOD FOR NUCLEAR IMAGING

The present disclosure relates to a device for endoscopic imaging and methods for imaging with a device for endoscopic imaging, specifically to a corresponding system with improved imaging.

BACKGROUND

High-quality imaging is of great interest for a wide range of applications. In the medical field in particular, where the health of the patient can depend on it, the best possible imaging is required for example as a basis for operations on the patient.

Normally, medical images are produced preoperatively, such as for example by means of computed tomography (CT), nuclear magnetic resonance tomography (NMR, MR, MRI, MRT), positron emission tomography (PET), single photon emission tomography (SPECT), ultrasound (US)—or on the other hand intra-operatively (io), such as for example by means of io CT, io MRI, io US or freehand SPECT. Recording of images is also known, for example the recording of an anatomical image (such as for example a CT-MRI or US image) using a functional image (such as for example a PET or SPECT image), i.e. an image which visualises the localised distribution of a function or a bodily activity. Such recorded images can for example help, in the case of tumour operations, to decide which tissue parts are to be excised on the basis of the anatomical and functional information. Images which are as up-to-date as possible and of the highest quality are desirable, as in such a manner it is possible to avoid damaging healthy tissue or not removing diseased tissue due to error.

Producing high-quality images places high requirements on detector data for imaging and on an evaluation system which must process these data. This is true in particular for the processing of detector data with movable detectors which are held/guided in the hand and/or which are located inside a cavity or a lumen of the body.

The prior art in the context of the present invention is disclosed for example in U.S. Pat. No. 6,602,488, U.S. Pat. No. 6,456,869, U.S. Pat. No. 6,317,622 or U.S. Pat. No. 6,167,296 and enables the tracking of hand-held probes as conventional diagnosis devices, in particular during a surgical intervention, and also tracking systems for determining the position and orientation of operating instruments and imaging devices.

The idea of tracking nuclear probes has already been disclosed in the past by a number of groups, for example as in U.S. Pat. No. 6,510,336 and U.S. Pat. No. 6,021,341. As furthermore disclosed in U.S. Pat. No. 6,643,538, nuclear probes can be designed to be integrated with a camera.

The output signal of nuclear probes is generally just a one-dimensional signal which is not temporally constant. The main advantages of such devices are the portability, simplicity and the possibility of the miniaturisation thereof for investigating cavities, for example when mounted on endoscopes. As each measurement is furthermore not limited to a certain position with respect to the preceding position, probes furthermore enable the scanning of any desired surfaces with a spatial precision which is only limited by the size of the sensor and the range of the detected nuclear radiation.

Nuclear probes, such as e.g. gamma and beta probes can measure the radioactive decay of radionuclides in tracers which are injected into the patient before the intervention. The disadvantage of these nuclear probes is the fact that one is concerned here with point measurements. This makes the weighting of the physical value on a surface more difficult if it changes considerably with position. A further problem in this case is the fluctuation of the measurement results, which is based on the statistical nature of the decay and detection process, which makes the interpretation of the measurement data difficult and potentially unreliable.

The use of probes of this type for combining position and orientation tracking with surface reconstruction and visualisation has been described in WO 2007/131561 A2. This method is known as freehand SPECT and is already used in the case of open surgical interventions, i.e. with the patient's body opened, and not by contrast in the minimally invasive field. Among other things, it includes measuring the emission of the target tissue using a nuclear probe with a detection characteristic essentially bundled in the longitudinal direction thereof, and also a comparison of this data with position information about the probe itself.

A disadvantage of all of the above-mentioned methods is the fact that the generally hand-guided nuclear probe delivers the data for an image calculated therefrom and that e.g. the quality of the image generated from the detected data may not be optimal or may be improvable due to a coincidentally unfavourable guiding of the probe by the user. This may be very difficult in the case of guiding endoscopic nuclear probes, where the movement options are very limited, inter alia due to guiding through the skin or through bodily orifices.

Against this background, the object of the present invention is to provide a system and method for intracorporeal imaging, particularly in the case of computer-controlled operation with nuclear probes, which delivers improved image quality compared to known methods.

Abstract

The above-discussed problems are solved at least to some extent by means of a system for endoscopic nuclear imaging according to Claim 1, an endoscopic nuclear probe according to Claim 23 and a method according to Claim 24.

In an embodiment, a system for endoscopic nuclear imaging is proposed. The system includes a movable endoscopic nuclear probe which includes a collimator and a detector for detecting radioactive radiation, wherein the endoscopic nuclear probe has an elongated body with a longitudinal axis (X), which is designed to be inserted into the body of a patient, wherein the detector and the collimator are arranged on the elongated body of the endoscopic nuclear probe, and wherein the collimator has a field of view with an axis (Y), wherein the axis (Y) of the field of view of the collimator is angled with respect to the axis (X) of the elongated body of the endoscopic nuclear probe. It further includes means for determining the position and orientation of the elongated body of the endoscopic nuclear probe; and an evaluation unit which includes: an interface system for transmitting data with information about the detected radioactive radiation, and information about the position and orientation of the elongated body of the endoscopic nuclear probe to the evaluation unit; a data storage section for storing the information; means for synchronising the information about the position and orientation of the elongated body of the endoscopic nuclear probe with the information about the radiation detected by the endoscopic nuclear probe; means for computationally determining an actual position and actual orientation of the elongated body of the endoscopic nuclear probe; a program storage section with a program for, if necessary, repeated determination of at least one quality value with regards to the imaging from the information mentioned.

An endoscopic nuclear probe is provided in a further embodiment. The probe includes an elongated body, a collimator, a detector for detecting radioactive radiation, wherein the endoscopic nuclear probe is set up to be inserted into the body of a patient using the elongated base body, and wherein the collimator is arranged at one end, and wherein the collimator has a field of view with an axis (Y), wherein the axis (Y) of the field of view of the collimator is angled with respect to the axis (X) of the elongated body of the endoscopic nuclear probe, so that the detection range of the probe for radioactive radiation lies in an angular region from 0 to 180 degrees with respect to the longitudinal axis, and wherein the detection characteristic is anisotropic with respect to a rotational symmetry about the longitudinal axis of the probe.

A method for endoscopic nuclear imaging is provided in a further embodiment. The method includes the insertion of a nuclear probe, which has a non-rotationally-symmetrical detection characteristic, into the body of a patient; recording radiation data by means of the nuclear probe; recording position and orientation data of the nuclear probe; calculating a three-dimensional image using the previously mentioned information; and calculating at least one quality value or parameter for the computed three-dimensional image.

Further features, aspects and details which can be combined with the embodiments described herein are disclosed in the dependent claims, the description and the figures.

SHORT DESCRIPTION OF THE FIGURES

A more specific description with reference to the embodiments of the invention is given so that the previously listed features can be understood better in detail. The attached figures relate to embodiments of the invention and are described briefly in the following.

DETAILED DESCRIPTION

The methods described herein use computer software to calculate various types of image information from detected information. The methods and algorithms used in the process are either known to the person skilled in the art or can be written, using standard expert knowledge, on the basis of the statements made herein. They are therefore not considered in detail.

The terms "Virtual Reality" (VR) and "Augmented Reality" (AR) are used in the following. Augmented Reality (also: Extended Reality) is understood to mean computer-assisted augmentation of the perception of reality. This is understood to include the enhancement of images or videos (of a patient's body) with computer-generated additional information or virtual objects by means of fade-in/overlay, that is to say here principally the image information computed from the nuclear probe data, e.g. of a radioactively marked tumour. By contrast, Virtual Reality is the illustration of reality and the physical characteristics thereof in a virtual environment computer-generated in real time. That is to say, VR operates generally only with "fully synthetically" generated/computed data and not with images from an imaging method, AR by contrast mixes both, real images and computer-generated images (also called "mixed reality"). The term "pose" is generally known as indicating both the (3D) position of an object in space and the orientation or location thereof. The term "quality value" or "quality parameter", here generally designated with Q, represents a parameter used in the context of this application which is suitable for representing the quality of the image depictions, representations etc. considered herein and for being processed in computer-assisted methods. In this case, Q can relate, depending on the method chosen as a basis, to a very wide range of mathematical values, as is described in more detail below, from (in a non-limiting list) scalars through vectors to matrices of any desired number of dimensions, vector fields or combinations of the aforementioned. The term "elongated body" used here in connection with the nuclear probe designates at least one part region of the probe and relates to the today practically continuous design of such probes for the medical field, which have a rod-shaped structure with the collimator at one end. This is not to be seen as a limitation however; rather a nuclear probe, as is suggested in embodiments, can absolutely also be realised as a non-elongated design with otherwise identical or similar functionality, which is therefore understood just as set out in the sense of the invention, even if the external shape is not to be designated exactly as elongated. Further, the tracking systems, probes, endoscopes, etc. described herein are connected via interfaces in each case to at least one evaluation unit, output unit and/or to one another. These interfaces known from the prior art can be connected via wireless radio systems or via wires, as is known from the prior art. Further, the means mentioned here for the purpose of computing 3D images, transformations, means for synchronisation, etc., can generally be realised as conventional computer systems (personal computers or workstations), on which algorithms in the form of computer programs are realised in accordance with the embodiments.

Figure 2:
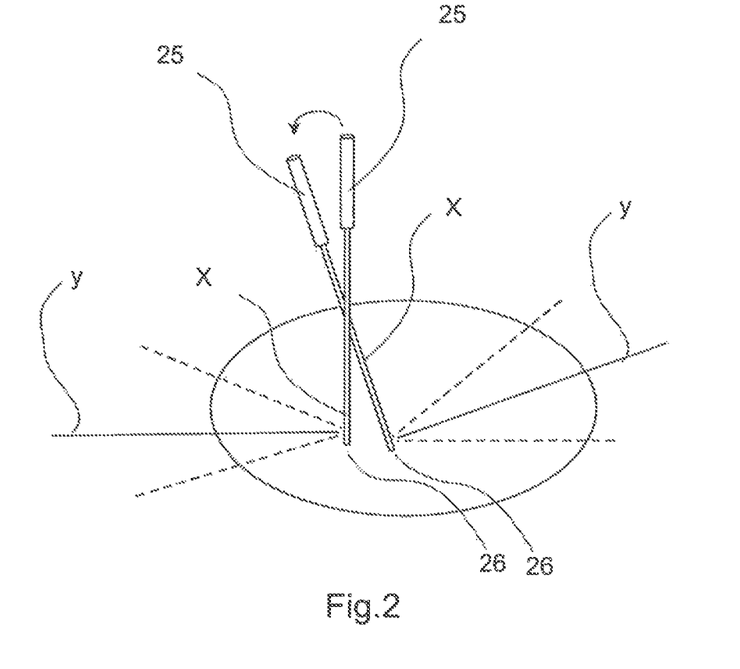
FIG. 2 schematically shows various orientations of a nuclear probe according to embodiments.

Embodiments relate to a system for nuclear imaging by means of an endoscopic nuclear probe, such as during an operative intervention on a patient. The nuclear probe has an anisotropic detection characteristic, so that only events from a certain solid angle range (see FIG. 2 and FIG. 8). During the measurement, which is typically carried out continuously, the detected values of the probe and/or the image calculated therefrom are regularly analysed and the quality of the image generated is expressed by calculating at least one quality parameter. These parameters can then be used for optimising the image, for example in order to notify the user that they should move the probe again to a different location/position for improving the recorded database. In a more complex variant, the quality assessment can be used to targetedly suggest a certain (or a plurality of different/alternative) position/location of the probe to the user, in order to increase the quality of the 3D image obtained from the probe data by means of a targeted location change of the probe by the user; further, the quality parameter can be used to change the position of the probe without the assistance of a user by means of actuators, for example by controlling a robot arm which guides the nuclear probe.

Figure 1:
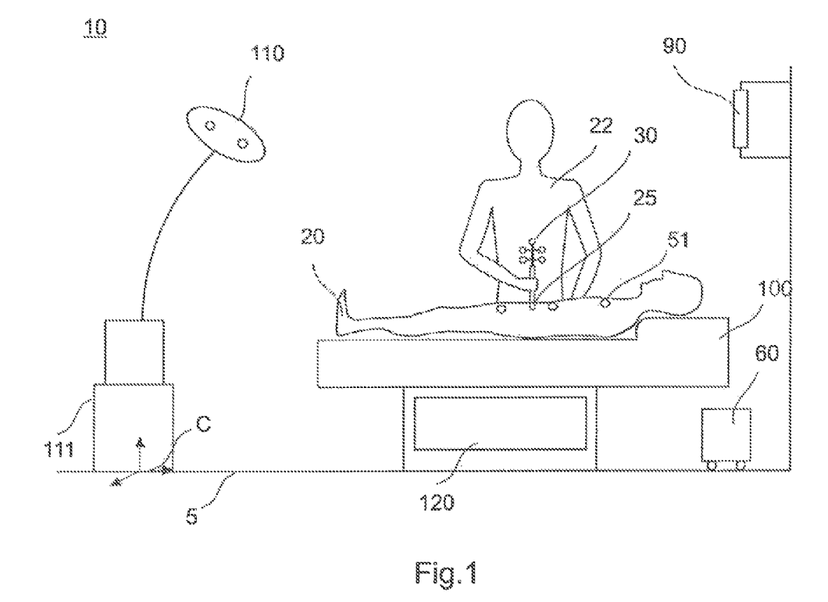
FIG. 1 shows a system according to embodiments.

A system 10 for endoscopic nuclear imaging is suggested, according to embodiments, as shown in FIG. 1. The patient 20 and the user 22 are not constituents of the system.

The movable endoscopic nuclear probe 25 includes a collimator and a detector for detecting radioactive radiation. The probe has an elongated body with a longitudinal axis (X) which is inserted into the body of a patient 20, for example through a trocar (not shown). In this case, the detector and the collimator 26 are arranged on the elongated body of the endoscopic nuclear probe 25. The collimator 26 has a field of view with an axis (Y), wherein the axis (Y) of the field of view is angled with respect to the axis (X) of the elongated body of the probe. This field of view is shown schematically in FIG. 2, the region between the dashed lines with centre axis y. In this case, the field of view is not only orientated in the lateral direction of the elongated body of the probe, but rather at the same time limited anisotropically onto an angular region with respect to the longitudinal axis X of the elongated body, similarly in an illustrative image to the light cone of a lighthouse.

Different technologies are considered as means for determining the position and orientation of the elongated body of the probe. An optical tracking system 110 is shown in FIG. 1, which detects or tracks one or a plurality of optical markers 30 and thus provides information about position and location of the probe.

The detected information of the nuclear probe 25 and the tracking system 110 are transmitted to an evaluation system 60. Data are transmitted via this interface system with information about the detected radioactive radiation of the nuclear probe, and also information about the actual position and actual orientation of the elongated body of the endoscopic nuclear probe. This can take place either in a wired manner or via radio interfaces (not illustrated) as in FIG. 1, radio and wired technologies can also be combined.

The evaluation unit 60 includes a data storage section for storing this information. The information about the position and orientation of the elongated body of the endoscopic probe are synchronised with the information about the radiation detected by the endoscopic nuclear probe by means of a synchronising unit, so that the evaluation unit 60 can link the radiation information with the location and orientation information, as a result of which a three-dimensional image of the radiation source can be computed by means of known algorithms (as for example in the case of the freehand SPECT image reconstruction mentioned at the beginning).

During the above process, an actual position and actual orientation of the elongated body of the endoscopic nuclear probe 25 can be computed from the data of the tracking system 110. A three-dimensional image of the distribution of the radiating material, i.e. typically a radioactive tracer located (injected) in the tissue of the patient which has accumulated in a tumour, can thus be computed by means of the data about the position and orientation of the nuclear probe 25 obtained in this manner and the measurement data delivered therefrom.

A quality parameter Q of the 3D image computed in this manner or the local distribution of the tracer material is then computed on the basis of predetermined algorithms after a certain measurement period or continuously. This parameter Q can e.g. take account of the number of detected radiation events (counts) from a certain volume or solid angle element and a certain direction, including the position and location data (=pose) of the probe. If, for example, markedly fewer events are detected from a certain direction than from an adjacent solid angle element in the certain direction, the radiation distribution computed for the first element is affected by a higher statistical error, or the achievable resolution for the first element is smaller.

There are various possibilities for computing the quality parameter Q or Q can, depending on the method, be e.g. a scalar, a vector, a scalar field, a vector field, a tensor or a 3D matrix. Q can e.g. express how large the variance is between the count rates from different solid angle elements for different directions in each case. Thus, the larger Q is in this case, the higher is the variance of the quality of the detected data between different solid angles or part volumes from certain directions, which is generally undesirable, as then certain part volumes e.g. exhibit too low and image resolution or too high an image noise. This would also mean that for a least one of the solid angle elements considered, the recording time is markedly lower compared to other regions, thus the quality of the illustration there is lower. Thus, if the variance Q on the entire image is too large in this case, the evaluation unit 60 decides that data must be collected retroactively. The region affected by this is then known from the preceding computing. Thus, the evaluation unit can compute in which direction data should again be collected with respect to the actual position of the nuclear probe, in order to improve the image quality or lower Q at the same time.

In embodiments, it is then possible to realise a plurality of options, depending on the computation and evaluation of Q (see below for further options for the properties of Q). In a simple variant, the user of the probe is signalled merely by binary signal (zero/one or also red/green), as to whether the already computed image fulfils the predetermined quality requirements. If this is not currently the case, a red indicator lamp/LCD, which can for example be attached on the probe or on the evaluation unit, can signal to the user that they should move the probe again without information about in which direction it should be moved or how it should be rotated. If the unit then determines that Q has reached a satisfactory value, the indicator changes to green. Of course, this signalling can take place in most different ways, e.g. also by means of an acoustic signal or by means of a corresponding voice output in the evaluation unit.

In a further variant, information about possible new poses of the probe is shared with the user by means of an output device, e.g. on an optical display, by means of a voice output or by means of haptic feedback at the probe. In a further variant, the computed correction information is used by the evaluation unit directly for controlling an actuator which changes the pose of the probe. This can be e.g. a robot arm which guides the probe, wherein the arm can at the same time include the sensor system for tracking the probe.

Quality criteria used in this case for the parameter Q can (in a nonlimiting manner) for example be:

a) the scaler density of information for different spatial elements (e.g. computed from the influence of the respective spatial element in the entire preceding data recording by means of the nuclear probe)—in this case Q is based on a 3D image or 3D scalar field a) the vectorial density of information for different spatial elements (e.g. computed from the directed influence of the respective spatial element in the entire preceding data recording by means of the probe)—in this case Q is based on a 3D vector field c) the separability of reconstructed structures in the respective spatial element, based on the hitherto recorded data—here Q is based on a 3D image, the sharpness of details and resolution capability of which is computed.

d) the condition number of the reconstruction system matrix, as is known to the person skilled in the art—in this case Q is a scalar.

e) the spectrum of the inherent values or singular values of the reconstruction system matrix—here Q is based on a vector.

Further methods for determining quality parameters Q of a completed-generated image from a nuclear probe are described in the German patent application 102008025151.8, for example on the pages 37 to 42, the teaching of which relating to this is hereby included by reference in full.

One of the above outlined handling instructions can then be chosen—i.e. signalling to the user whether to move further or not; outputting one or a plurality of new desired poses or the vectors which lead to these poses; or controlling one or a plurality of actuators for moving the probe—depending on whether a possible improvement of at least one part region of the image results from the computed Q according to one of the above or similar methods or methods derived therefrom.

In the case of the option of outputting the desired pose or the corresponding movement information from the information derived from Q, a desired position and desired orientation of the elongated body of the endoscopic nuclear probe 25 is then computed; as described above with the additional condition that a corresponding position change of the nuclear probe leads to an improvement of the quality value Q; which at the same time should mean or means an increase of the image quality. By means of an output system, e.g. the optical display 90, the computed desired information is output to a user following conversion to instructions for moving the endoscopic nuclear probe. a possible corresponding illustration is shown in FIG. 3.

To determine the desired values mentioned for the pose of the nuclear probe 25, a plurality of information can be used, such as the movement volume in which the nuclear probe can be moved, the possible directions into which the nuclear probe can be directed (inter alia dependent on the anatomy of the patient known due to the preoperative image data), the location or pose of the patient and the organs in the body, the expected radiation distribution in the body, etc. This information can be obtained from preoperative data of the patient (recorded or not), statistical models, information of the movement of the nuclear probe or further endoscopic instruments, etc. This information can for example be used to check the plausibility of the desired values or to weight the same. Thus, for example it must be ensured that a pose in which the location of the probe would overlap with an organ is not suggested.

The output system 90 is typically a screen, but can also include a multiplicity of other variants, e.g. a voice output system or a haptic output by means of force feedback via actuators in the nuclear probe, for example in the handle. In this manner, the user can move the probe to the desired position and desired orientation in accordance with the transmitted information, so that additional events can improve the count rate for the relevant solid angle.

Figure 3:
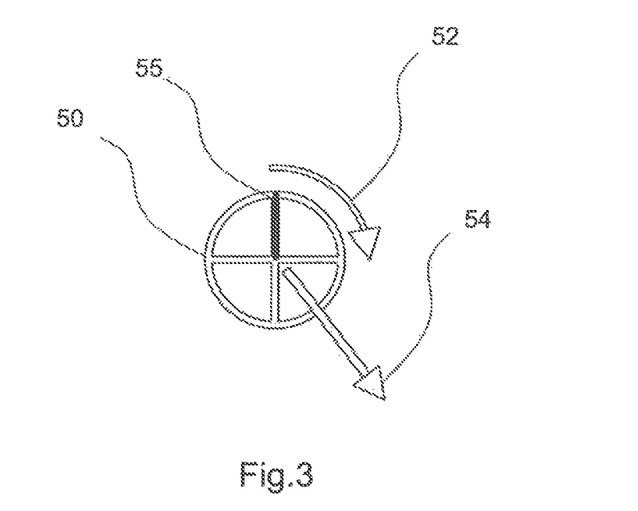
FIG. 3 shows an illustration of setpoint position and location data on a display according to embodiments.

An example for the representation of correction information to a user 22, which is typically depicted on the display 90, is shown in FIG. 3. The circle with the cross 50 in this case symbolises the probe and the marking 55, the orientation of the same with respect to the longitudinal axis thereof. The round arrow 52 indicates to the user how the probe should be rotated about its longitudinal axis and the linear arrow 54 shows a displacement, that is to say that the user should move the handle in this direction. The display can in reality react to actions of a user, so that in the event of correct movement, the corresponding arrows become smaller and disappear when the new desired position is reached. In the event of incorrect or not quite correct movement by the user, it may by contrast be the case that an arrow becomes larger or the direction changes. In the embodiments described below, the correction information can flow directly into the control of one of the robot arms holding the probe, so that the human factor is eliminated as a source of error.

As shown in FIG. 1, the optical tracking system has a coordinate system C. The location of the operating table 100 with respect to the tracking system is typically known or can be measured in advance. If the patient 20 lies in a defined manner on the OP table and is immovable, for example because they are anaesthetised or fixed, and the operating table is fixed with respect to the tracking system, it is therefore possible to assume a stationary location of the patient 20. It is necessary to know the exact external dimensions of the patient or the location thereof on the table 100 and their exact position in order to compute imaging by means of the detector data of the probe in a combination with, for example, preoperative images, such as for example CT images. If the location of the patient is not included in the method, the computed 3D image, for example of a tumour, is depicted on a screen 90 without reference to the body of the patient. The tracking system 110 can be realised in embodiments also in any desired tracking technologies, for example as electromagnetic tracking system, as a mechanical tracking system (such as for example in the case of robot systems or in the case of positioning arms), as an acceleration-sensor or gyroscope based tracking system, as a sonic tracking system, as an ultrasound tracking system, or as a radioactive tracking system or RF-based system.

One possibility for using preoperative data, for example computed tomography (CT) or nuclear magnetic resonance (MRI) images in this method would be to record these prior to the operation with a marker provided and during the above-described application of the method, to bring the same into alignment with at least one marker 51 (see FIG. 1) on the body of the patient computationally in the evaluation unit 60.

A further option for using preoperative data in this method would be the intraoperative recording of the surface of the patient by means of an optical or haptic scanning system and the recording of this surface with the surface of the patient computed from the preoperative data. The optical tracking system 110 from FIG. 1 can also be designed to this end at the same time.

In embodiments, at least one reference is fixed in the form of at least one marker 51 on the patient 20 or in relation to the patient. The position of this reference is determined during the application of the method according to the invention via means for determining the position and orientation of the reference. This means can for example be an optical tracking system, thus for example the tracking system 110 can also expediently be used for location determination of the marker(s) 51 as reference(s). The information about the location of the reference(s) (and if appropriate the orientation thereof, e.g. in the case of spatially expanded, non-punctiform markers) is transmitted via interfaces (radio interfaces in FIG. 1) to the evaluation unit 60.

These position and location data of the reference are synchronised by and in the evaluation unit 60 with the other data processed in the system, namely location and position of the nuclear probe and also the count information of the probe. In this manner, even a position change of the patient 20 during an operation can be taken into account. The recording of the various information, that is to say count information of the nuclear probe, the position and location information thereof by means of the tracking system 110 and also if appropriate the position information of the patient 20 via the references 51 are in this case typically detected continuously and synchronised with one another. The 3D image information computed from the count rates of the probe and the location or position data can in this case be overlaid with any desired images of the body of the patient and output on a screen 90 (or for example 3D glasses). Such preoperative data can e.g. be CT images or MRI images. In order to bring the same into line with the image data of the probe, that is to say to synchronise the data in such a manner that e.g. a radioactively marked tumour detected by the nuclear probe is faded into the CT image at the correct point, the evaluation unit 60 determines the actual position and actual orientation of the elongated body of the nuclear probe 25 relative to the reference or the markers 51 constantly or at regular intervals.

The output system 90 of the evaluation unit 60 can therefore be designed for outputting a three-dimensional reproduction of the information about the actual position and actual orientation of the elongated body of the endoscopic nuclear probe 25 and the information about the actual position and actual orientation of the reference 51 and/or information about the detected radiation.

The output system 90 is typically a display which can be a visual display, a haptic display, an acoustic display or a combination of a plurality of these displays. In particular, the display can be set up as described above to reproduce instructions to a user. These typically include reference to a further desired position and desired orientation of the elongated body of the elongated body of the endoscopic nuclear probe, in order to improve the current data situation or to deliver corresponding correction instructions for moving the probe 25 as illustrated in FIG. 3.

The endoscopic nuclear probe 25 is in this case typically designed for detecting the radioactive radiation of a radioactive marker in the interior of a body, preferably detecting gamma radiation, beta radiation or both.

During the computation of possible desired positions and desired orientations of the nuclear probe, in embodiments, the position of a trocar, through which the probe is inserted into the body of the patient, or generally possible movements of the nuclear probe in the body can be taken into account. If, for example, the probe is inserted into a cavity within the body, so that the part of the probe including the detector/collimator moves in the cavity, the information about the cavity can be taken into account during the computing of possible alternative positions. This information can for example be extracted from the preoperative image data by means of the evaluation unit. In addition, typical possible movement parameters of the probe with respect to the trocar can be stored in the evaluation unit. A similar strategy can even be derived from the preceding movements of the nuclear probe without detecting the position of the trocar.

The detection field of the nuclear probe 25 can be arranged in any desired section of the angular region from 0 to 180 degrees, as non-limiting examples e.g. 0 degrees to 90 degrees, 0 degrees to 120 degrees, or 10/20 degrees to 180 degrees. In embodiments, the nuclear probe can be used in an endoscope, wherein the endoscope can (in a non-limiting manner) be a laporoscope, a laryngoscope, a rhinoscope, an arthroscope, an epiduroscope, an oesophagoscope, a gastroscope, an enterescope, an anoscope, a colonoscope, a sigmoidoscope, a proctoscope, a cystoscope, a gynoscope, a colposcope, a hysteroscope, a falloposcope, a bronchoscope, a thoracoscope, a mediastinoscope, an otoscope, or a ductoscope. The non-definitive list is fundamentally valid for all of the endoscopes mentioned in this document.

Figure 4:
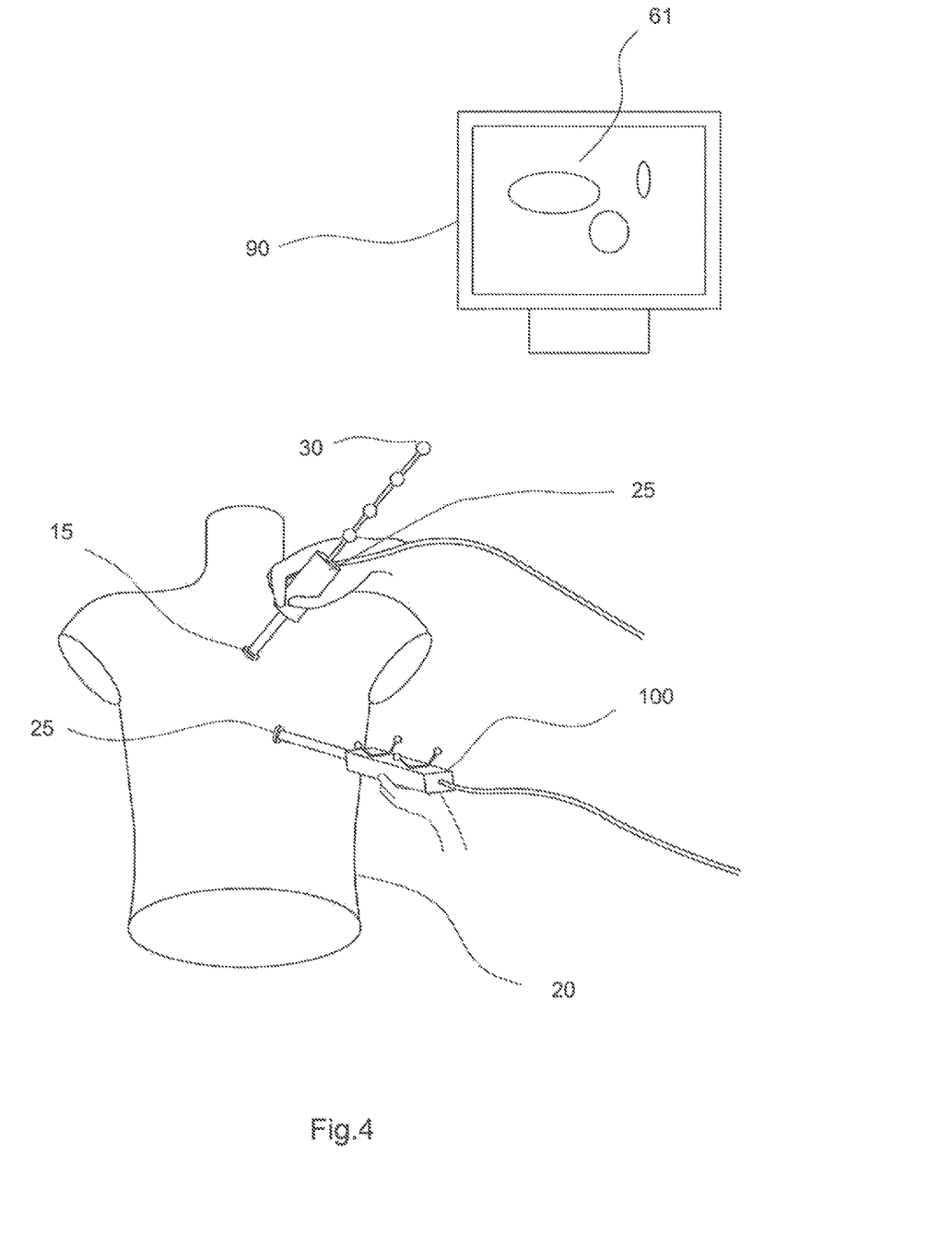
FIG. 4 shows the application of a system according to embodiments.

In addition to the endoscopes at least one further positioned white-light and/or a fluorescent endoscope 100 can be used, which transmits optical information to the evaluation system, that is to say to the evaluation unit 60, see FIG. 4. The information thereof can be output via a visual display 90, in order to generate virtual or augmented reality depictions of three-dimensional images and instructions to the user from the perspective of this white-light and/or fluorescent endoscope 100. That is to say, the image information of the additional endoscope(s) 100 are used as a possible image source, which can be depicted with the image information from the nuclear probe 25 and optionally with further preoperative images 61.

The virtual reality of one of the positioned endoscopic instruments 100 depicted on a display 90, either the additional optical or the nuclear probe 25, can be depicted in embodiments in relation to the three-dimensional images from the perspective of the respective other. In this case, the image information obtained with the nuclear probe can also be depicted combined visually with ultrasound images, wherein the additional endoscopic instrument 100 is consequently an endoscopic ultrasound probe. A prerequisite for the image merging mentioned and the detection of additional position and orientation information and also patient and organ locations is a calibration of the position, orientation and equivalent optics of the nuclear probe with the respective additional image detection systems. This can take place by design by means of decoupled phasing in of the additional image detection systems, by means of calibration means on the basis of known structures (such as for example calibration phantoms) or any desired combination of those previously mentioned.

In the embodiments, the imaging system according to the invention can contain a further external detector 120 (see FIG. 1) outside of the patient 20. This is preferably a gamma camera or a PET or Compton camera which operates in coincidence with the detector of the endoscopic nuclear probe 25. Thus, additional information for generating the three-dimensional reproduction can be provided, wherein the external detector is preferably arranged below (see FIG. 1), above or at the side of the patient 20 or around the patient 20.

If the system 10, as already described above, is also set up for reproducing preoperatively obtained image data, these data can preferably be depicted from the perspective of one of the endoscopic instruments 100 mentioned—or these data can be used as a template for generating the three-dimensional reproduction.

Figure 5:
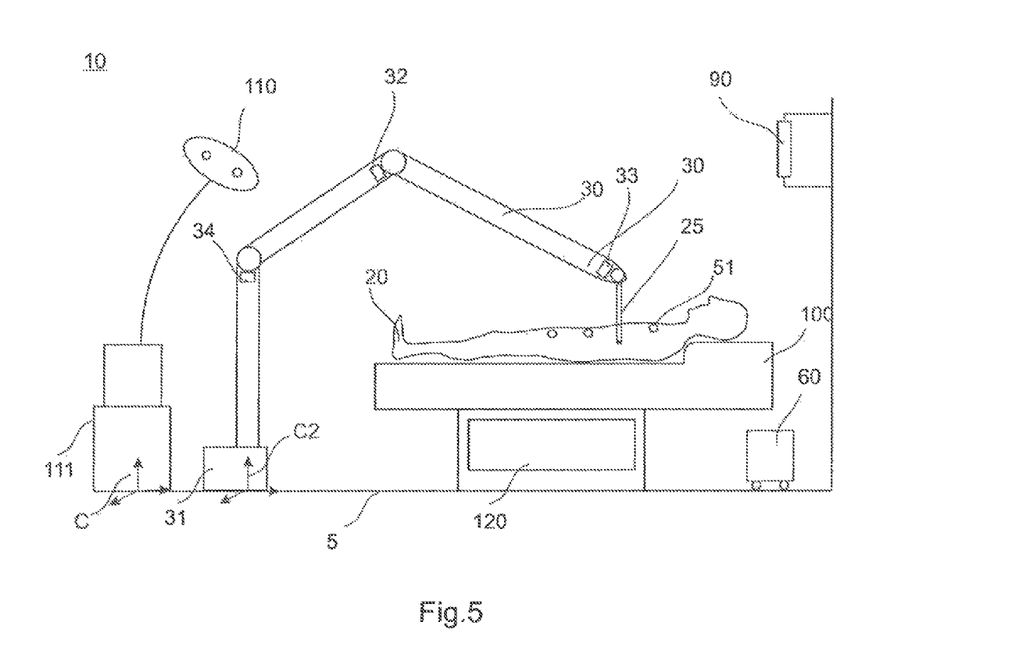
FIG. 5 shows a further system according to embodiments.

In embodiments, as shown in FIG. 5, the nuclear probe can also be held or guided by a robot arm 30. The robot arm is in this case typically connected, for example via radio interface, to the evaluation unit 60, so that the possible new desired position data and desired location data are transmitted directly from the evaluation unit 60 as control data to the robot arm which executes the movements, in order to thus improve the imaging by means of the nuclear probe 25. Furthermore or alternatively thereto, one or a plurality of the endoscopic instruments 100 can also be held by a second robot arm. The arm has sensors 32, 33, 34 for detecting the location of the probe 25. The coordinate system C2 thereof (it is clear to the person skilled in the art that coordinate systems can be used here in any desired manner, as long as the relationship to one another is known) is used as a reference for the location of the probe 25. The system 110 can here be used for recording the position and surface of the patient 20.

In embodiments, the endoscopic nuclear probe can be inserted into an endoscope. Typical endoscopes for this purpose are (in a non-limiting manner) a laporoscope, a laryngoscope, a rhinoscope, an arthroscope, an epiduroscope, an oesophagoscope, a gastroscope, an enterescope, an anoscope, a colonoscope, a sigmoidoscope, a proctoscope, a cystoscope, a gynoscope, a colposcope, a hysteroscope, a fallopo-scope, a bronchoscope, a thoracoscope, a mediastinoscope, an otoscope, or a ductoscope.

Figure 6:
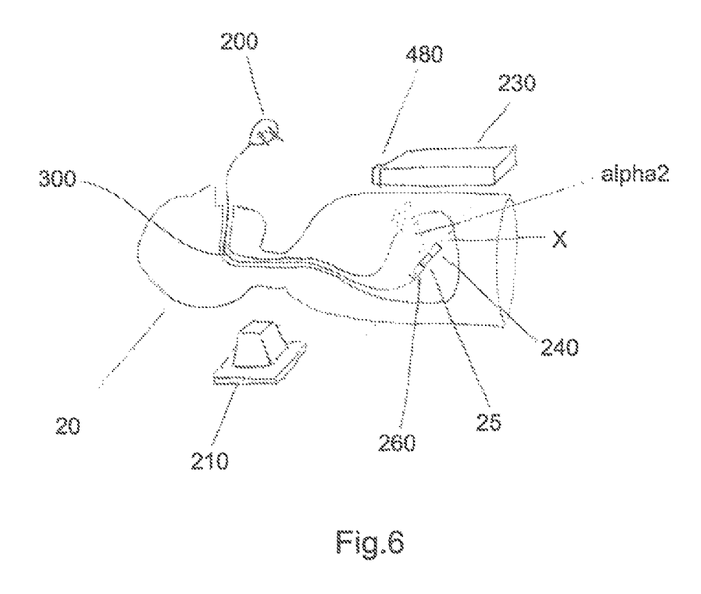
FIG. 6 shows a further system according to embodiments.

FIG. 6 shows an embodiment, in which the nuclear probe 25 is located completely in the patient 20 and is moved/orientated from the outside by means of a mechanical or electric control 200 by means of a gastroscope 300. An e.g. electromagnetic tracking system 210 monitors the location of the nuclear probe which has an axis X and a three-dimensional field of view alpha2. A gamma camera 230 can operate in coincidence with the nuclear probe 25. The probe 25 is provided with an electromagnetic sensor 240 for the tracking. It additionally has an additional ultrasonic transmitter and probe 260, in order to generate additional image information. The nuclear probe is an elongated body at the end of the endoscope (gastroscope) 300 which is inserted through the oesophagus. In this endoscopic system (with a gastroscope), which is electromagnetically tracked, a gamma camera 230 is therefore above the patient, in addition to the nuclear probe in the endoscope, which gamma camera supplies further information for the imaging. In this case, the nuclear probe (the elongated body at the end of the gastroscope 300) and the gamma camera 230 are tracked by the system 210.

Figure 7:
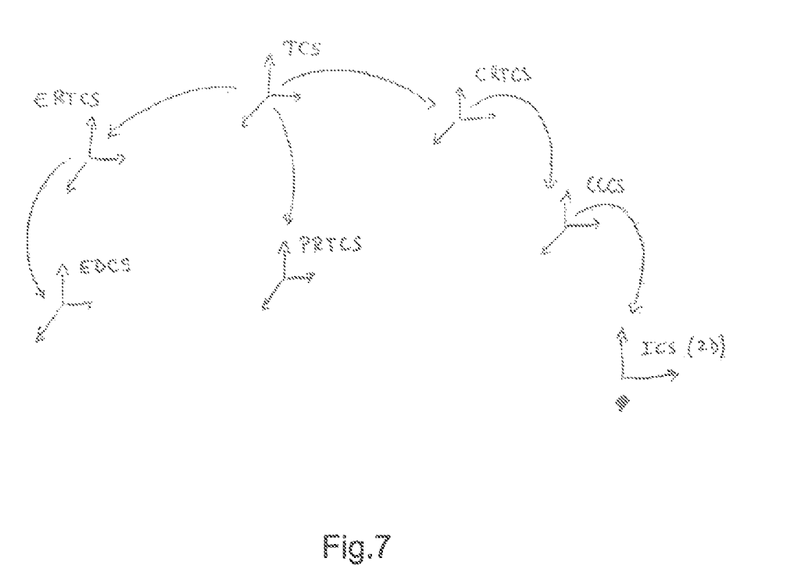
FIG. 7 shows a transformation method according to embodiments.

The computing of the relative pose (=position and orientation) of the nuclear probe with respect to the reference 51 (on the patient, see for example FIG. 1) is in FIG. 7. This takes place via transformation matrices in homogeneous coordinates, at which a 3D point is depicted as a 4D vector. Each of these 4×4 matrices is characterised as "T". The direction of the transformation is from the coordinate system at bottom right in the direction of the coordinate system at top left. The different coordinate systems are also depicted as 3 arrows, as here all are 3D coordinate systems. The coordinate systems are designated as follows:

TCS=Tracking (System) Coordinate System
RCS=(Patient) Reference Coordinate System
PCS=(Nuclear) Probe Coordinate System
DCS=Detector Coordinate System The transformation PCS_T_TCS and the transformation RCS_T_TCS are delivered by the tracking system 110, 210 (cf FIG. 1, FIG. 6) in real time. The transformation DCS_T_PCS is determined by a one-time calibration "hand-eye calibration".

Figure 8:
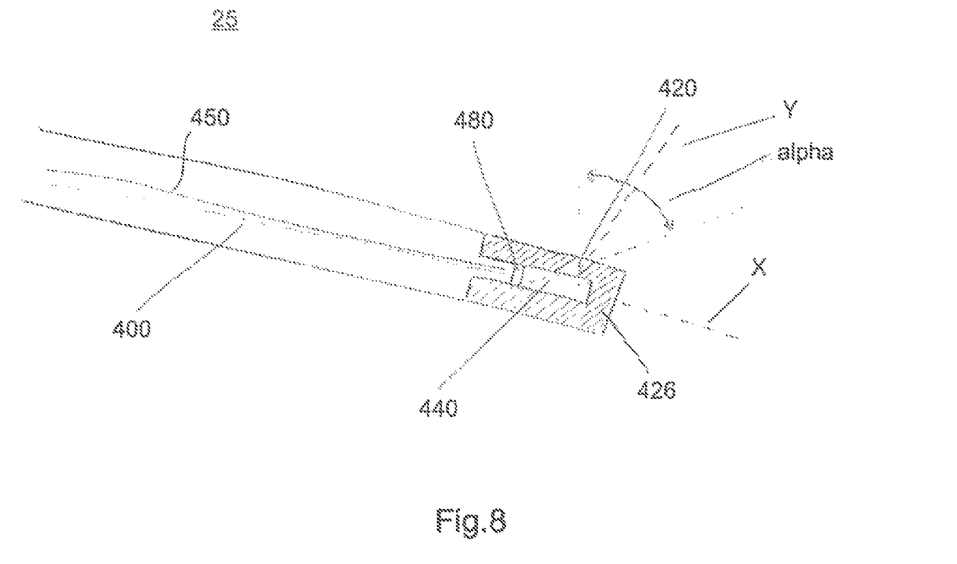
FIG. 8 shows a nuclear probe according to embodiments.
Figure 9:
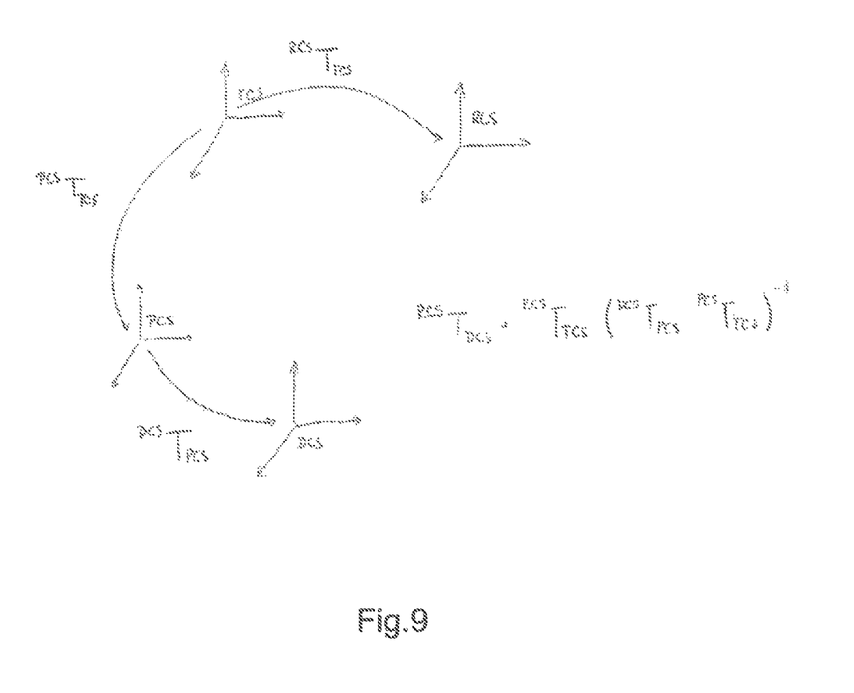
FIG. 9 shows a transformation method according to embodiments.

A typical laparoscopic nuclear probe 25 according to embodiments is shown in FIG. 8, as is shown for example in FIG. 1 and FIG. 9. It includes a housing 400, at the end of which a tungsten collimator 26, 426 is attached. The probe has a longitudinal axis X. The collimator has a laterally directed opening 420 which delimits the detection angle alpha or determines the detection characteristic through a field of view. A scintillator crystal 440 is located in the collimator 426, 26. The laparoscopic gamma probe shown has a window with an opening angle of approx. 70 degrees. The silicon photomultiplier 480 in addition to the scintillator crystal 440 converts the incident light generated by the scintillator into electricity. The silicon photomultiplier is connected to the outside world via a cable 450. The field of view with the opening angle or angle range alpha has a central axis Y which has inclined towards the longitudinal axis X of the probe.

FIG. 9 shows the coordinates which are required in order to depict the 3D nuclear image of a system (as in FIG. 1) into the perspective of a further video endoscope (which delivers a 2D image, as possible for example in FIG. 4). The tracking system (with coordinate system TCS), the pose of the nuclear probe reference target 30 (coordinate system ERTCS), the patient reference target 51 (coordinate system PRTCS) and the video endoscope reference target (CRTCS, not depicted, in FIG. 4 inside the body). By calibrating the nuclear probe 25, one obtains the pose of the detector (coordinate system EDCS). By means of calibration, the pose of the camera centre of the video endoscope (coordinate system CCCS) and the pose of the image plane (ICS) result. In this case, it is to be taken into account that the coordinate system of the video image is only in 2 dimensions. Thus, the transformation of CCCS to ICS is a projection from 3D to 2D, that is to say a 3×4 matrix.

Figure 10:
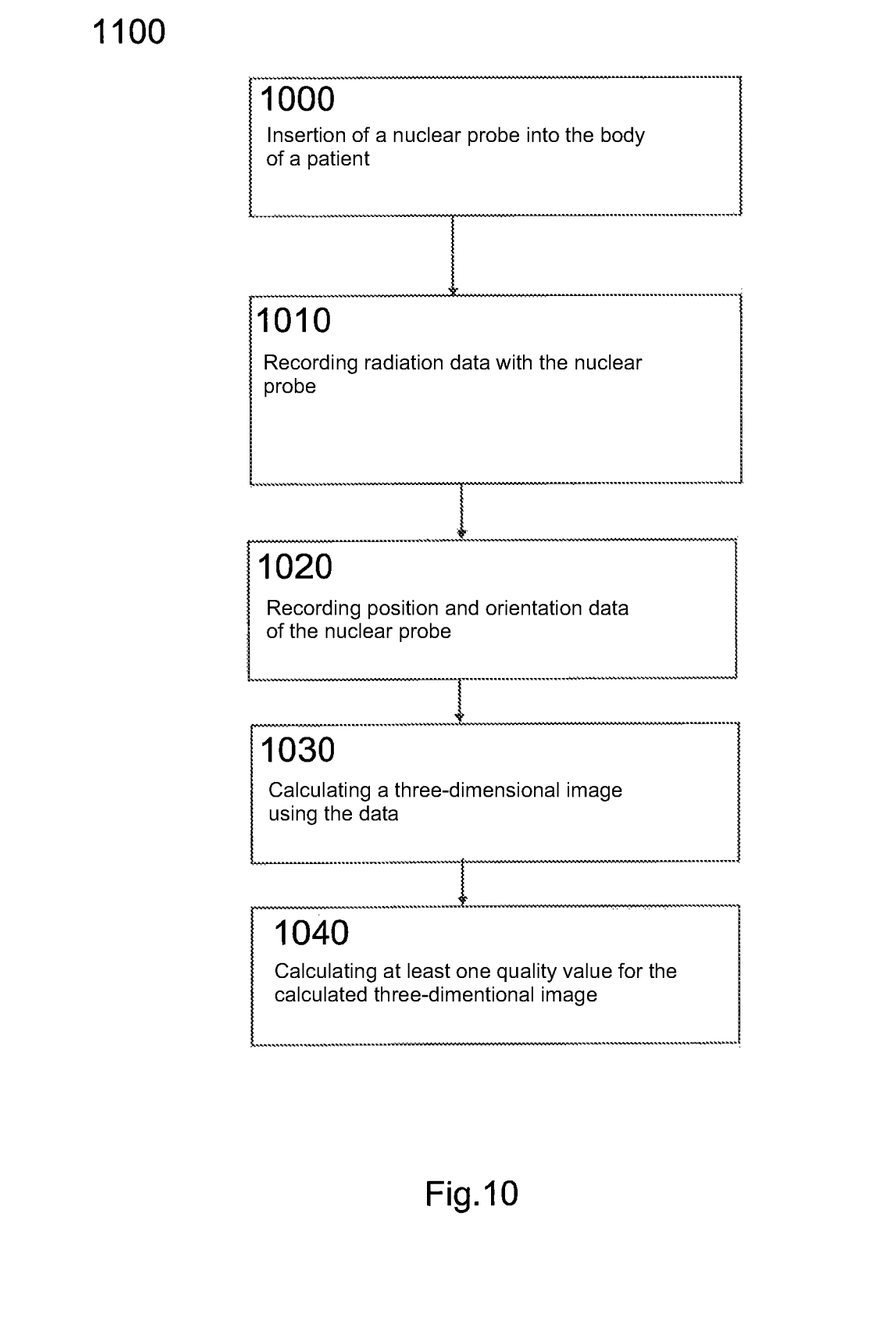
FIG. 10 shows an imaging method according to embodiments.

FIG. 10 shows a method 1100 according to embodiments. It includes the insertion of a nuclear probe into the body of a patient in block 1000; recording radiation data by means of the nuclear probe in block 1010; recording position and orientation data of the nuclear probe in block 1020; calculating a three-dimensional image using the previously mentioned information using the data in block 1030; and calculating at least one quality value for the computed three-dimensional image in block 1040. Then, it may follow according to embodiments: the displaying of binary information—whether the probe should be moved further or not—to a user who guides the probe; or the displaying of suggestions for possible movements of the nuclear probe and/or the displaying desired coordinates and a desired location of the probe (combined: desired pose) and/or the control of an actuator, preferably of a robot arm in order to change the pose and the probe.

Whilst the preceding is directed, other and further embodiments of the invention can be set up by combining those described without deviating from the protective scope of the invention, which is determined by the following claims.

The invention claimed is:

1. A system for endoscopic nuclear imaging, which comprises:
    a movable endoscopic nuclear probe which includes a collimator, a crystal for detecting radioactive radiation, and a photomultiplier coupled to the crystal, wherein the endoscopic nuclear probe has an elongated body with a longitudinal axis (X), which is designed to be inserted into the body of a patient, wherein the crystal and the collimator are arranged on the elongated body of the endoscopic nuclear probe, wherein the collimator surrounds the crystal and the photomultiplier, wherein the collimator has a laterally directed opening which delimits a detection angle through a field of view of the collimator, and wherein the field of view has an axis (Y), wherein the axis (Y) of the field of view of the collimator is inclined with respect to the axis (X) of the elongated body of the endoscopic nuclear probe, and wherein the field of view of the collimator is limited anisotropically with respect to the longitudinal axis X of the elongated body;
    means for determining the position and orientation of the elongated body of the endoscopic nuclear probe; and
    an evaluation unit, which includes:
        i) an interface system for transmitting data with information about the detected radioactive radiation, and information about the position and orientation of the elongated body of the endoscopic nuclear probe to the evaluation unit;
        ii) a data storage section for storing the information;
        iii) means for synchronising the information about the position and orientation of the elongated body of the endoscopic nuclear probe with the information about the radiation detected by the endoscopic nuclear probe;

iv) means for computationally determining an actual position and actual orientation of the elongated body of the endoscopic nuclear probe;
v) a program storage section with a program for repeated determination of at least one quality value Q with regards to the imaging from the information mentioned; and
vi) an output system for outputting a three-dimensional reproduction of the information about the actual position and actual orientation of the elongated body of the endoscopic nuclear probe and information about the detected radiation.

2. The system according to claim 1, wherein the evaluation unit further comprises:
means for computing a desired position and desired orientation of the elongated body of the endoscopic nuclear probe, wherein these data are determined under the additional condition that a corresponding placing of the elongated body of the endoscopic nuclear probe leads to an improvement of the at least one quality value Q; and
an output system for outputting an instruction to a user or robot for moving the endoscopic nuclear probe to the desired position and desired orientation.

3. The system according to claim 1, further comprising:
a reference which is fixed in relation to the patient; and
means for determining the position and orientation of the reference, wherein the interface system of the evaluation unit is further designed for transmitting data with information about the position and orientation of the reference to the evaluation unit, wherein the means for synchronising the evaluation unit are further designed for synchronising the information about the position and orientation of the reference, wherein the evaluation unit has means for determining an actual position and actual orientation of the elongated body of the endoscopic nuclear probe relatively to the reference, and wherein the output system of the evaluation unit is further designed for outputting a three-dimensional reproduction of the information about the actual position and actual orientation of the elongated body of the endoscopic nuclear probe and the information about the actual position and actual orientation of the reference and/or information about the detected radiation.

4. The system according to claim 3, further comprising a display for depicting the three-dimensional reproduction generated.

5. The system according to claim 4, wherein the display is selected from the group consisting of a visual display, a haptic display, an acoustic display and a combination of a plurality of these displays.

6. The system according to one of claim 4, wherein the display is further set up to reproduce instructions to a user.

7. The system according to claim 6, wherein the instructions comprise the reference to a further possible desired position and desired orientation of the elongated body of the endoscopic nuclear probe.

8. The system according to one of claims 1 to 2, wherein the endoscopic nuclear probe is in this case designed for detecting the radioactive radiation of a radioactive marker in the interior of a body.

9. The system according to claim 2, wherein the means for computing additional possible desired positions and desired orientations of the elongated body of the endoscopic nuclear probe takes into account information relating to the position of a trocar and/or possible movements of the endoscopic nuclear probe in the computing.

10. The system according to claim 2, wherein the means for computing additional possible desired positions and desired orientations of the elongated body of the endoscopic nuclear probe, with respect to the reference, takes into account information relating to the position of a trocar and/or possible movements of the endoscopic nuclear probe in the computing.

11. The system according to claim 1 or 2, wherein the field of view of the collimator provides a detection field of the endoscopic nuclear probe that can be angled in any desired section of an angular region from 0 to 180 degrees with respect to the longitudinal axis (X).

12. The system according to claim 1 or 2, wherein the endoscopic nuclear probe can be used in an endoscope, wherein the endoscope is a laporoscope, a laryngoscope, a rhinoscope, an arthroscope, an epiduroscope, an oesophagoscope, a gastroscope, an enterescope, an anoscope, a rectoscope, a colonoscope, a sigmoidoscope, a proctoscope, a cystoscope, a gynoscope, a colposcope, a hysteroscope, a falloposcope, a bronchoscope, a thoracoscope, a mediastinoscope, an otoscope, or a ductoscope.

13. The system according to claim 1, wherein the system further comprises a positioned white-light, a fluorescent endoscope, or a visual display for virtual or augmented reality depictions of three-dimensional images and instructions to the user from the perspective of this white-light and/or fluorescent endoscope.

14. The system according to claim 1 or 2, wherein the system further comprises a further positioned endoscopic instrument and a visual display for depicting virtual reality and instructions from the perspective thereof.

15. The system according to claim 13, wherein the virtual reality of one of the positioned endoscopic instruments in relation to the three-dimensional images can be depicted from the perspective of the respective other, and wherein optionally one of the endoscopic instruments contains an ultrasound probe, so that computed image information of the ultrasound probe can be depicted together with the image information of the nuclear probe on a display.

16. The system according to claim 1 or 2, wherein the system furthermore contains an external detector which operates in coincidence with the crystal, which provides additional information for generating the three-dimensional reproduction.

17. The system according to claim 1, wherein the system is furthermore set up for reproducing preoperatively obtained images.

18. The system according to claim 1, further comprising a robot which holds the endoscopic nuclear probe.

19. The system according to claim 1, further comprising a robot which holds one or a plurality of the endoscopic instruments.

20. The system according to claim 3, wherein the means for determining the actual position and actual orientation of the elongated body of the endoscopic nuclear probe is an electromagnetic system, an optical tracking system, a mechanical tracking system, an acceleration-sensor or gyroscope based tracking system, a sonic tracking system, an ultrasound tracking system, or a radioactive tracking system or RF-based system.

21. The system according to claim 8, wherein the detecting the radioactive radiation comprises detecting gamma radiation, beta radiation, or both.

22. A method for endoscopic nuclear imaging, comprising:
inserting a nuclear probe, which has a non-rotationally-symmetrical detection characteristic, into the body of a patient, wherein the nuclear probe includes a collimator, a crystal for detecting radioactive radiation, and a photomultiplier coupled to the crystal, wherein the endoscopic nuclear probe has an elongated body with a longitudinal axis (X), wherein the collimator surrounds the crystal and the photomultiplier, wherein the collimator has a laterally directed opening which delimits a detection angle through a field of view of the collimator, wherein the field of view has an axis (Y), wherein the axis (Y) of the field of view of the collimator is inclined with respect to the axis (X) of the elongated body of the endoscopic nuclear probe;

continuous recording of radiation data by means of the nuclear probe;

continuous recording of position and orientation data of the nuclear probe, continuous computing of a three-dimensional image using the previously mentioned information;

continuous computing of at least one quality value for the computed three-dimensional image.

23. Method according to claim 22, further comprising:
computing at least one desired position and desired orientation of the elongated body of the nuclear probe using the above-listed information, with the additional condition that a further recording of radioactive data leads with the specification of the new desired values to an improvement of the at least one quality value.

24. The method according to claim 22 or 23, further comprising:
recording position data of the body of the patient.

25. The method according to claim 22, further comprising:
outputting an instruction to a user for moving the elongated body of the endoscopic nuclear probe to the desired position and desired orientation;
recording additional data by means of the nuclear probe with the new position data;
re-computing of the three-dimensional image and the quality value,
outputting the image on a display.

* * * * *